US011150694B2

(12) United States Patent
Markovsky et al.

(10) Patent No.: US 11,150,694 B2
(45) Date of Patent: Oct. 19, 2021

(54) FIT SYSTEM USING COLLAPSIBLE BEAMS FOR WEARABLE ARTICLES

(71) Applicant: Microsoft Technology Licensing, LLC, Redmond, WA (US)

(72) Inventors: Igor Markovsky, San Jose, CA (US); Tzu-Yuan Lin, San Jose, CA (US); Vijay Boovaragavan, Cupertino, CA (US); Michael Nikkhoo, Saratoga, CA (US); Brian Toleno, Cupertino, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 312 days.

(21) Appl. No.: 15/603,359

(22) Filed: May 23, 2017

(65) Prior Publication Data

US 2018/0341286 A1  Nov. 29, 2018

(51) Int. Cl.
| | | |
|---|---|---|
| *G06F 1/16* | (2006.01) | |
| *A42B 3/12* | (2006.01) | |
| *A61F 9/02* | (2006.01) | |
| *A45F 5/00* | (2006.01) | |
| *G02B 27/01* | (2006.01) | |

(52) U.S. Cl.
CPC .............. *G06F 1/163* (2013.01); *A42B 3/12* (2013.01); *A42B 3/127* (2013.01); *A45F 5/00* (2013.01); *A61F 9/026* (2013.01); *G02B 27/0176* (2013.01); *G06F 1/1637* (2013.01)

(58) Field of Classification Search
CPC ......... A42B 3/063; A42B 3/064; A42B 3/065; A42B 3/10; A42B 3/124; A42B 3/14; A42B 3/30; A41D 13/015; A41D 13/0518; A63B 71/08; G06F 1/163; G06F 1/1637; G02B 27/0176
USPC ............................................................. 2/411
See application file for complete search history.

(56) References Cited

U.S. PATENT DOCUMENTS 4,646,367 A * 3/1987 El Hassen ................ A42B 3/00
                                                          2/171
5,038,782 A    1/1991 Gevins et al.
(Continued)

FOREIGN PATENT DOCUMENTS

EP      3367159 A1    8/2018
SE      449054 B      4/1987
(Continued)

OTHER PUBLICATIONS

"International Search Report and Written Opinion Issued in PCT Application No. PCT/US18/028977", dated Jul. 9, 2018, 12 Pages.
(Continued)

*Primary Examiner* — Anne M Kozak
(74) *Attorney, Agent, or Firm* — Alleman Hall Creasman & Tuttle LLP

(57) ABSTRACT

Disclosed is a fit system for improving users' comfort with wearable articles, such as head-worn articles. The fit system includes a lattice of collapsible beams that can be constructed of elastomer foam located at the interface between the wearable article and a part of the user's body. The collapsible beam construction provides a non-linear relationship between the amount of force or pressure applied on the body part and the amount of compression of the foam.

17 Claims, 9 Drawing Sheets

(56) References Cited

U.S. PATENT DOCUMENTS

| | | | | |
|---|---|---|---|---|
| 5,025,504 | A | * | 6/1991 | Benston .................. A42B 3/10 2/181.4 |
| 5,030,501 | A | * | 7/1991 | Colvin ................ B65D 65/406 428/178 |
| 5,561,866 | A | * | 10/1996 | Ross ...................... A42B 3/065 2/410 |
| 5,930,840 | A | | 8/1999 | Arai |
| 5,946,734 | A | * | 9/1999 | Vogan ...................... A42B 3/00 2/171 |
| 5,950,243 | A | * | 9/1999 | Winters ................ A42B 3/065 2/411 |
| 6,314,586 | B1 | * | 11/2001 | Duguid ................ A42B 3/069 2/411 |
| 6,332,227 | B1 | * | 12/2001 | Fang ...................... A42B 3/145 2/183 |
| 6,654,960 | B2 | * | 12/2003 | Cho .................. A63B 71/1225 2/22 |
| 6,751,811 | B1 | | 6/2004 | Hill |
| 6,752,450 | B2 | * | 6/2004 | Carroll, III .............. B32B 3/28 188/371 |
| 7,424,967 | B2 | * | 9/2008 | Ervin ...................... A47J 36/02 228/193 |
| 7,802,320 | B2 | * | 9/2010 | Morgan ................ A42B 3/128 2/411 |
| 8,155,496 | B1 | * | 4/2012 | Cumberland ......... F41H 5/0414 385/147 |
| 8,465,825 | B1 | * | 6/2013 | Cumberland ........... F16D 65/12 165/DIG. 533 |
| 8,533,869 | B1 | * | 9/2013 | Capuano ................ A42B 3/12 2/171 |
| D837,455 | S | * | 1/2019 | Dickie ........................ D29/102 |
| 2002/0017805 | A1 | * | 2/2002 | Carroll, III ............. F16F 7/121 296/187.03 |
| 2004/0061663 | A1 | | 4/2004 | Reynolds et al. |
| 2004/0250340 | A1 | * | 12/2004 | Piper ...................... A42B 3/064 2/411 |
| 2005/0251898 | A1 | * | 11/2005 | Domingos ............. A63B 71/10 2/412 |
| 2006/0075693 | A1 | * | 4/2006 | Tsunoda ............... B31D 3/0207 52/80.1 |
| 2007/0013611 | A1 | * | 1/2007 | Nakabayashi ......... G02B 7/002 345/8 |
| 2007/0226881 | A1 | * | 10/2007 | Reinhard ............... A42B 3/322 2/412 |
| 2007/0238379 | A1 | * | 10/2007 | Bhatnagar ............. F41H 5/0457 442/135 |
| 2008/0066217 | A1 | * | 3/2008 | Depreitere ............. A42B 3/064 2/412 |
| 2008/0172779 | A1 | * | 7/2008 | Ferguson ................ A42B 3/124 2/455 |
| 2011/0289662 | A1 | | 12/2011 | Neary |
| 2013/0019384 | A1 | * | 1/2013 | Knight .................. A42B 3/064 2/411 |
| 2013/0042397 | A1 | * | 2/2013 | Halldin ................. A42B 3/064 2/411 |
| 2013/0152287 | A1 | * | 6/2013 | Cormier ................. A42B 3/124 2/459 |
| 2013/0313765 | A1 | | 11/2013 | Anderson et al. |
| 2014/0013492 | A1 | * | 1/2014 | Bottlang ................ A42B 3/125 2/414 |
| 2014/0098009 | A1 | | 4/2014 | Prest et al. |
| 2014/0109304 | A1 | * | 4/2014 | Kwan .................. A41D 13/015 2/461 |
| 2014/0115761 | A1 | | 5/2014 | McNeal et al. |
| 2014/0129938 | A1 | | 5/2014 | Tang |
| 2015/0000018 | A1 | * | 1/2015 | Brandt ............... A41D 13/0156 2/455 |
| 2015/0047113 | A1 | * | 2/2015 | Stringfellow .......... A42B 3/124 2/455 |
| 2016/0062454 | A1 | | 3/2016 | Wang et al. |
| 2016/0255900 | A1 | * | 9/2016 | Browd ...................... A42B 3/14 |
| 2016/0302507 | A1 | * | 10/2016 | Lewis ....................... F41H 1/08 |
| 2016/0334628 | A1 | | 11/2016 | Lyons |
| 2016/0345095 | A1 | * | 11/2016 | Gamper ............... H04R 5/0335 |
| 2016/0353825 | A1 | * | 12/2016 | Bottlang .................. B32B 3/12 |
| 2016/0370587 | A1 | | 12/2016 | Roberts |
| 2016/0377872 | A1 | * | 12/2016 | Hurbi ................. G02B 27/0172 359/630 |
| 2017/0053445 | A1 | * | 2/2017 | Chen .................... H04N 13/344 |
| 2017/0332070 | A1 | * | 11/2017 | Markovsky ............ H01L 22/32 |
| 2018/0027676 | A1 | * | 1/2018 | Araki ...................... G06F 3/067 |
| 2018/0035739 | A1 | * | 2/2018 | Cohen ................ H01L 51/0096 |
| 2018/0055102 | A1 | * | 3/2018 | Desnoyers ......... A41D 13/0156 |
| 2018/0092420 | A1 | * | 4/2018 | Lewis ...................... B32B 7/08 |
| 2018/0140037 | A1 | * | 5/2018 | Frieder, Jr. ............ F41H 5/0457 |
| 2018/0264718 | A1 | * | 9/2018 | McCluskey ............. B29C 35/02 |
| 2018/0364491 | A1 | * | 12/2018 | Park ........................ G06F 3/011 |
| 2018/0373327 | A1 | * | 12/2018 | Todeschini ......... G02B 27/0093 |
| 2018/0376626 | A1 | * | 12/2018 | Hurbi ...................... G06F 1/163 |
| 2019/0137762 | A1 | * | 5/2019 | Hu ...................... G02B 27/144 |
| 2019/0388782 | A1 | * | 12/2019 | Lee .......................... A42B 3/30 |

FOREIGN PATENT DOCUMENTS

| | | |
|---|---|---|
| WO | 2014082023 A1 | 5/2014 |
| WO | 2016070188 A1 | 5/2016 |

OTHER PUBLICATIONS

"Oculus Rift CV1 Teardown", https://www.ifixit.com/Teardown/Oculus+Rift+CV1+Teardown/60612, Published on: Mar. 30, 2016, 15 pages.

"Office Action Issued in European Patent Application No. 18725705.0", dated Jan. 29, 2021, 4 Pages.

* cited by examiner

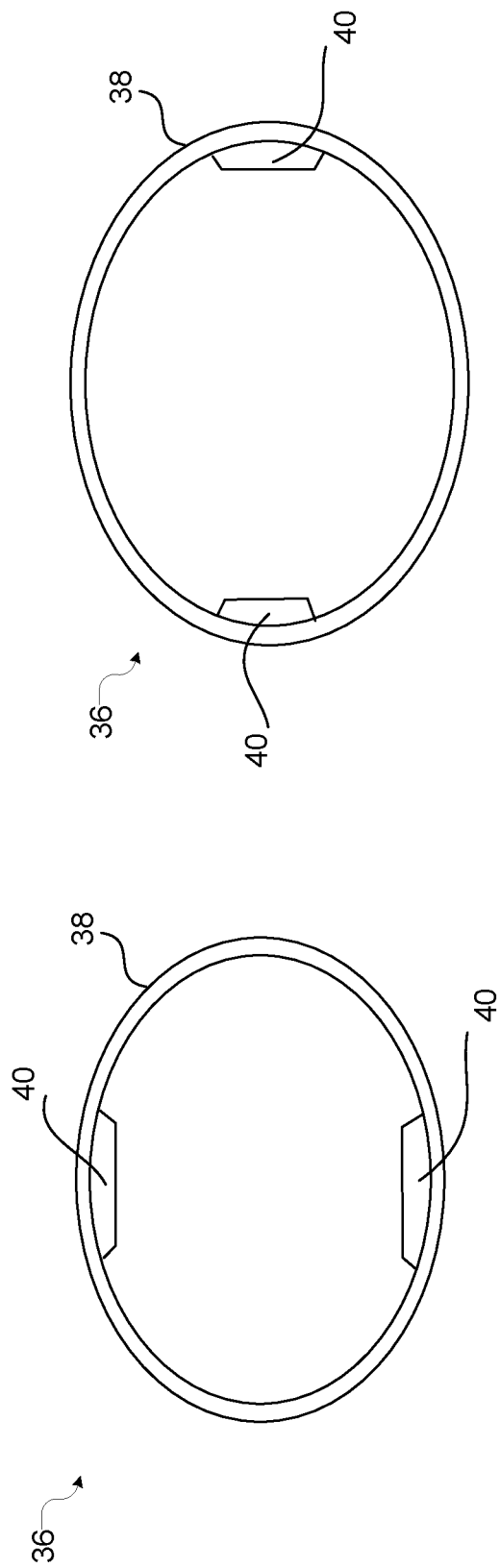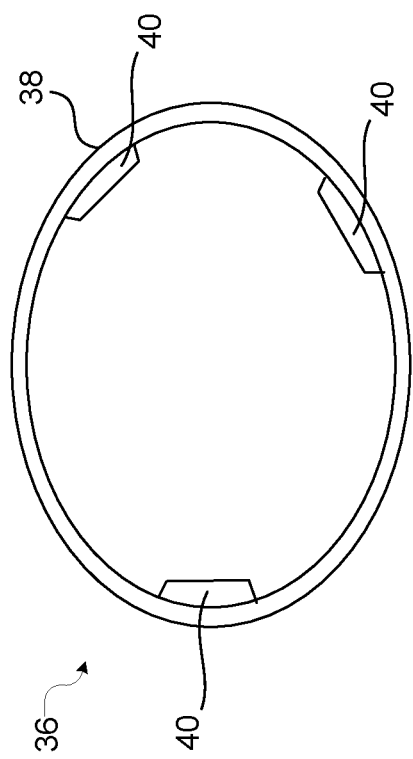
FIG. 5A
FIG. 5B
FIG. 5C

FIT SYSTEM USING COLLAPSIBLE BEAMS FOR WEARABLE ARTICLES

TECHNICAL FIELD

This disclosure relates to comfort fit systems for wearable articles, and more particularly, to cushioning material constructed of collapsible beams for wearable articles.

BACKGROUND

The human head comes in many shapes and sizes and can vary significantly from person to person. In particular, human heads include variably shaped skulls, bumps, depressions, and variable amounts of hair. Human heads also tend to be quite sensitive to force or pressure. One-size-fits-all wearable articles (e.g., armbands, bicycle helmets, head mounted displays, headphones, or masks) struggle with granular adjustment. To enable a snug fit, many wearable articles are lined with foam on their surfaces that contact the head. While worn, the foam compresses to the shape of the wearer's head. However, as the foam compresses, the reactive pressure or force on the wearer's head increases. The increased pressure can cause discomfort to the wearer, especially if the article is worn for a prolonged period.

SUMMARY

Introduced herein is a fit system including cushion material mounted on a wearable article for the head ("head article") exhibiting a substantially constant reactive pressure in response to compression of the cushioning material for a specified range of compression values. The cushioning material is applied to a rigid frame of articles such as helmets, head mounted displays, or masks.

In some embodiments, the wearable can comprise a rigid frame configured to be worn by a user on the user's head, and a cushion material mounted to the rigid frame. The cushion material may be positioned against the user's head when the wearable is worn by the user. The cushion material includes a repeating pattern of collapsible beams that causes the cushion material to produce a substantially constant reactive pressure in response to compression of the cushion material over a specified range of compression values.

Other aspects of the disclosed embodiments will be apparent from the accompanying figures and detailed description.

This Summary is provided to introduce a selection of concepts in a simplified form that are further explained below in the Detailed Description. This Summary is not intended to identify key features or essential features of the claimed subject matter, nor is it intended to be used to limit the scope of the claimed subject matter.

BRIEF DESCRIPTION OF THE DRAWINGS

One or more embodiments of the present disclosure are illustrated by way of example and not limitation in the figures of the accompanying drawings, in which like references indicate similar elements.

FIG. 5A is a top view of a head article featuring two fit system pads on either side of the user's head.

FIG. 5B is a top view of a head article featuring two fit system pads on the front and back of the user's head.

FIG. 5C is a top view of a head article featuring three fit system pads positioned about the user's head.

DETAILED DESCRIPTION

Figure 1:
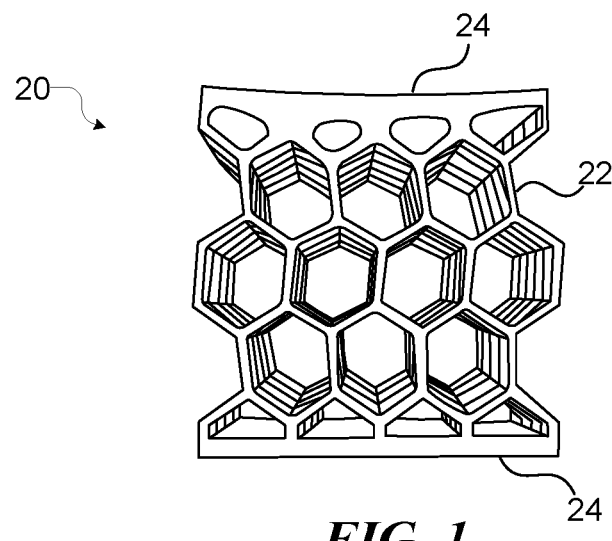
FIG. 1 is an illustration of cushioning material of the fit system including collapsible beams in a repeating pattern in an uncompressed state.

To achieve a snug fit of a wearable article without increasing discomfort to the wearer, a fit system including collapsible beams is disclosed. The fit system is a foam or foam-like material that uses a lattice structure made of the collapsible beams. Upon receiving a threshold of compressive pressure, beams within the lattice structure buckle and become compromised. The lattice is intended to collapse one layer at a time in response to varying levels of compression. The amount of pressure required to increase compression after the beams within the lattice have become compromised is zero or negligible until all layers in the lattice have collapsed. In this manner the fit system is able to adjust to physical variance between wearers without correspondingly increasing or decreasing snugness of fit. The fit system is installed on one-size-fits-all wearable articles (e.g., armbands, athletic pads, bicycle helmets, head mounted displays, headphones, or masks).

In this description, references to "an embodiment," "one embodiment" or the like mean that the particular feature, function, structure or characteristic being described is included in at least one embodiment introduced here. Occurrences of such phrases in this specification do not necessarily all refer to the same embodiment. On the other hand, the embodiments referred to also are not necessarily mutually exclusive.

The figures and related text of this document describe certain embodiments of a fit system for an article to be worn on the head ("head article") suitable for use in near-to-eye display (NED) systems, helmets, masks, or caps. The following description generally assumes that a "user" of a head article is a human. Note, however, that a head article of the disclosed embodiments can potentially be used by a user that is not human, such as a machine or an animal. Hence, the term "user" can refer to any of those possibilities, except as may be otherwise stated or evident from the context.

This disclosure makes often reference to "collapsible beams." Collapsible beams are similar to trusses. Structures made of collapsible beams, as the term is used herein, are intended to buckle or collapse under compressive pressure and to reform (revert back to their normal, uncollapsed state)

when the pressure is removed. A truss is generally a structure that includes two-force members only, where the members are organized so that the assemblage as a whole behaves as a single object. A "two-force member" is a structural component where force is applied to only two points. Although this definition allows the members to have any shape connected in any stable configuration, trusses typically are combined to form a number of polygonal units constructed with straight members whose ends are connected at joints referred to as nodes.

In this context, external forces and reactions to those forces are considered to act only at the nodes and result in forces in the members that are either tensile or compressive. A planar truss is one where all members and nodes lie within a two dimensional plane, while a space truss has members and nodes that extend into three dimensions. Various embodiments of collapsible beam construction as disclosed here may be in planar or space configurations.

Lattices and other beam structures include a number of properties that determine the effect of forces on the structure. In general terms, the properties are used to determine the general strength of the structure. These properties include the length of each beam, the diameter of each beam, and the support condition of each node. Beam strength has an inverse relationship with length, and a direct relationship with diameter. The particular function for each respective relationship varies based on support condition.

Support condition refers to the manner that each node connects beams together. Support condition is not a numeric value, rather, it is a design scheme, and many schemes are possible. For the purposes of this disclosure each support condition is a scheme of fixed support. With respect to collapsible beam structures, exemplary support conditions include atomic or molecular lattices of solid substances (e.g., a lattice of silicon atoms in a solid state, or a molecular H2O 'ice' lattice). Other examples include polygonal lattices that fit within a vertical plane. In some embodiments, the collapsible beams may have varying lengths, diameter, and support conditions across a repeating pattern of a lattice.

FIG. 1 is an illustration of a cushioning material of the fit system 20 including multiple collapsible beams 22 formed in a repeating pattern (lattice) and in an uncompressed state. In this illustration, the collapsing beams are organized into a repeating hexagon pattern. Each side of a hexagonal unit is a collapsible beam. The support condition of each node in the repeating collapsible beam lattice includes three beams in a single plane (i.e., the plane of the figure), each 120° apart, and a fourth and fifth beam perpendicular to the other three beams. An alternative embodiment of a node may be tetrahedral (four beams, any two of which are 120° apart in a single plane). Another example of a node may include eight beams, any two of which are either 90° or 180° apart in a single plane.

On either side of the fit system 20 from the collapsible beams 22 are contact surfaces 24. The contact surfaces 24 are positioned to contact respectively a frame of the head article and a lining facing the head of the wearer. When compressive forces are applied to the contact surfaces 24, the collapsible beams 22 begin to buckle. When a collapsible beam 22 buckles, the behavior of compressive force becomes disproportionate with respect to reactive pressure. This is to say that a graph describing reactive pressure as a function of compression distance becomes relatively flat (horizontal) in a specified range of compression values. The flat portion is disproportionate in the sense that one factor changes while the other remains substantially constant.

Figure 2:
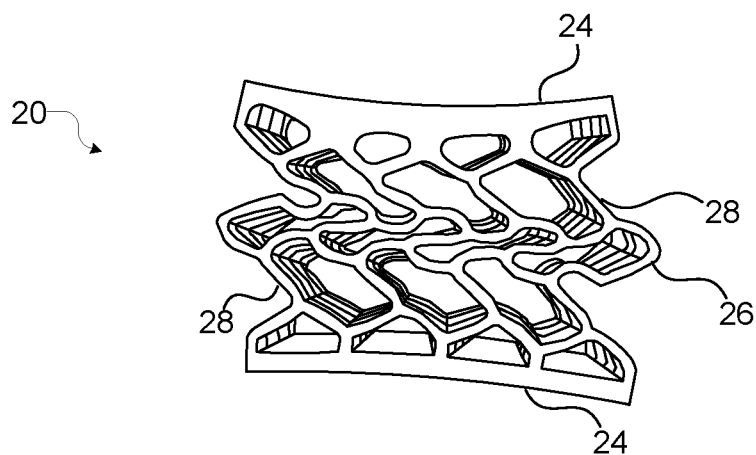
FIG. 2 is an illustration of cushioning material of the fit system of FIG. 1 in a compromised state including a single collapsed layer.

FIG. 2 is an illustration of cushioning material of the fit system of FIG. 1 in a partially collapsed state including a single collapsed layer. When compressive forces (not shown) are applied, the collapsible beams 22 buckle in layers. Herein FIG. 2 collapsed layer 26 is positioned between two compromised layers 28. The fit system 20 has received enough compressive force to compromise each layer. Additional compression does not require additional pressure to maintain a greater state of compression once the layers have become compromised.

As compression is increased, the compromised layers 28 fully collapse similarly to collapsed layer 26. Compromised layers 28 have almost no resistance to compression. The resistance to compression is not precisely zero; however, on a scale of tenths of pounds per square inch ("PSI"), or pressure that a human sensory system can detect, the resistance is negligible. When all layers are fully collapsed, additional compression is met with notable increased pressure.

Figure 3:
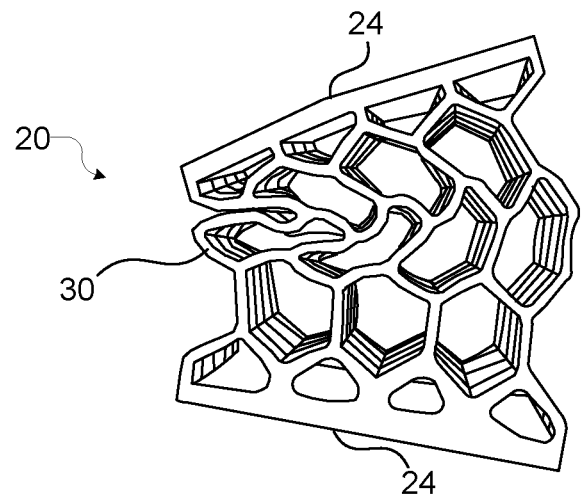
FIG. 3 is an illustration of cushioning material of the fit system of FIG. 1 in a compromised state including a collapsed corner.

FIG. 3 is an illustration of cushioning material of the fit system 20 of FIG. 1 in a partially collapsed state including a collapsed corner. An entire layer will not necessarily collapse across the entire fit system 20. Where compressive forces are applied to only part of contact surfaces 24, layers will partially collapse. Where fit system 20 comprises a long strip of cushioning material contacting the wearer's head, it is beneficial to be able to partially collapse the fit system 20. Partially collapsed layers 30 enable granular fit adjustment for small changes in the user's head such as bumps, thick patches of hair, or other pressure points.

The fit system 20 is thus able to adjust across an entire span of cushioning material between a thickness where layers are compromised and a thickness where all layers are collapsed while retaining a substantially constant reactive pressure. In some embodiments, and depending on overall thickness of the cushioning material, the range having substantially constant reactive pressure is between 10 mm and 25 mm. In some embodiments, the cushioning material retains substantially constant reactive pressure in response to compression force over a compression range of 12 mm. In some embodiments, the substantially constant reactive pressure is between 2-10 kPa. In some embodiments, the substantially constant reactive pressure is 0.5 PSI+/−0.1.

In some embodiments, the cushioning material is made of elastomer foam. The collapsible beam construction of the cushioning material can be made with a 3-D printer, for example. A number of suitable 3-D printing techniques are discussed in the following US patents: "Method and apparatus for three-dimensional fabrication", U.S. Pat. No. 9,211,678, granted Dec. 15, 2015, "Continuous liquid Interphase printing", U.S. Pat. No. 9,205,601, granted Dec. 8, 2015, "Method and apparatus for three-dimensional fabrication with feed through carrier", U.S. Pat. No. 9,216,546, granted on Dec. 22, 2015. The techniques in the cited patents are particularly useful for printing the collapsible beam lattices disclosed herein.

For additional user comfort or aesthetic reasons, the fit system 20 can include a covering fabric or fabrics (not pictured) wrapped around the cushioning material. Additionally, a silver coating can be applied to or included in the fabric for antibacterial requirements.

Figure 4:
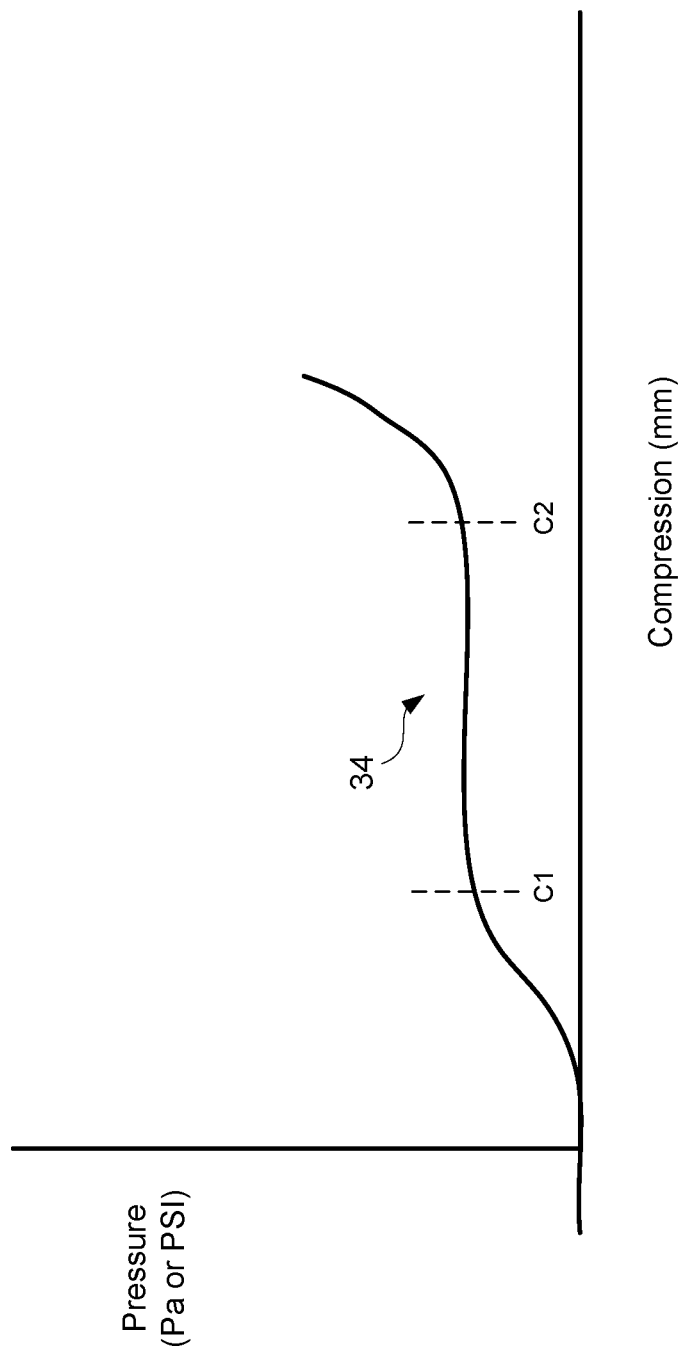
FIG. 4 is a graph illustrating a nonlinear pressure versus compression curve.

FIG. 4 is a graph illustrating a nonlinear pressure versus compression curve. The graph is representative of the pressure profile of the fit system 20. Upon the application of pressure (left side of graph), the fit system 20 begins to compress. Initially, there is a proportional relationship between compression and reactive pressure. At the compression value C1 where the layers within the cushioning material become compromised, the required pressure to continue compressing the cushioning material levels off such that almost no additional pressure is necessary. This trend continues until compression value C2, where all layers of the cushioning material have collapsed. Between compression value C1 and C2 reactive pressure does not increase proportionately to compression. After compression value C2 the proportional relationship between compression and reactive pressure resumes. The disproportionate zone 34 of the graph represents the zone of fit adjustment for the head article. The placement of the disproportionate zone 34 along both axes will depend on the specific application for which the cushioning material is intended to be used.

As discussed above, the design choices in this regard include length of each beam, diameter of each beam, and support condition of each node. The positioning of the disproportionate zone 34 is preferably at a pressure value that is comfortable for the user, and spans a compression range typical of bumps, depressions, and disproportionate hair growth in human heads. In some embodiments, it is comfortable for user to have 0.5 PSI of pressure, where 12 mm is suitable variance for granular fit adjustments. Some embodiments of the head article also have a gross fit adjustment mechanism for larger variances in head size, such as between child and adult.

FIGS. 5A, 5B, and 5C are top views of a head article featuring a number of configurations of fit system pads. The head article 36 includes a rigid frame 38. In FIG. 5, the rigid frame 38 is has a ring shape; however, many other shapes are possible and would depend on the particular nature and purpose of the head article 36. In some embodiments, different fit system pads 40 positioned about the user's body may be designed with different values for the constant pressure. For example, a first pad may be designed with a structure that maintains 0.5 PSI, and a second pad, on the same article, may be designed with a structure that maintains 0.75 PSI (or another value). In FIG. 5A, the head article 36 further includes two fit system pads 40. The fit system pads 40 are positioned on either side of the user's head. In the embodiment of FIG. 5B, two fit system pads 40 are positioned to contact the front and back sides of the user's head. In each embodiment of FIGS. 5A and 5B, the fit system pads 40 are positioned opposite one another for a secure fit on the user's head.

In the embodiment of FIG. 5C, there are three fit system pads 40. The three fit system pads 40 are positioned in an offset pattern. Two of the three fit system pads 40 are on either the front or backsides of the user's head. In many embodiments, increasing the number of fit system pads 40 increases the ability of the fit system 20 to secure to a user's head.

Figure 6A:
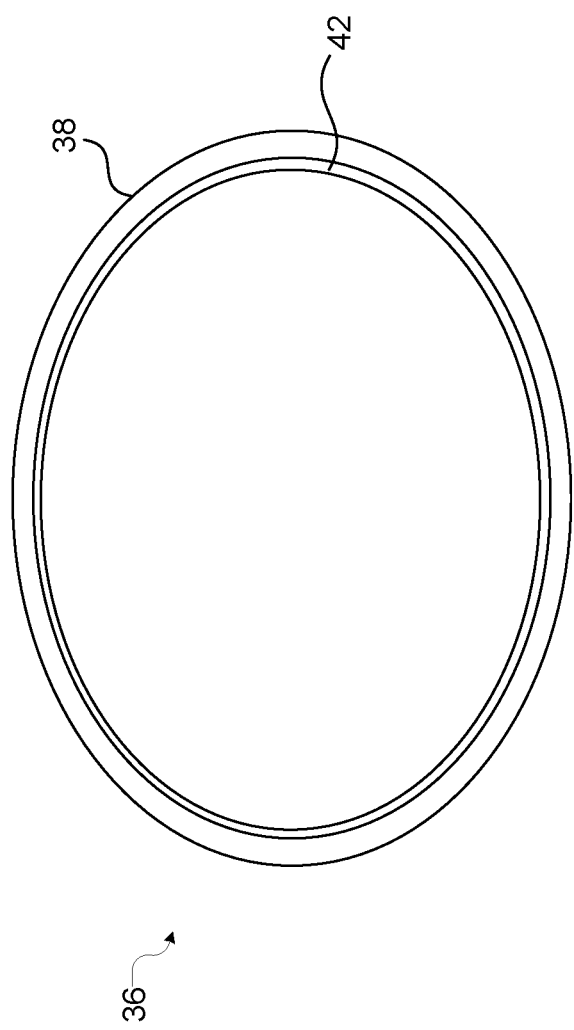
FIG. 6A is a top view of a head article featuring a loop fit system.

FIG. 6A is a top view of a head article featuring a loop fit system 42 In some embodiments, the head article 36 uses a loop fit system 42 rather than individual fit system pads 40. In these embodiments, the loop fit system 42 lines the inside of a rigid frame 38 and, while worn, tracks the circumference of the user's head. Depending on the shape of the rigid frame 38, the loop fit system 42 may be constructed to compensate for the curvature of the fit system.

Figure 6B:
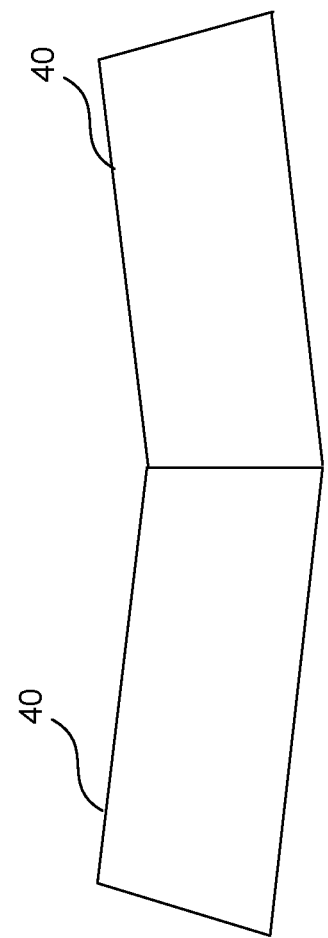
FIG. 6B is an illustration of two fit system pads positioned so as to shape an arc.

FIG. 6B is an illustration of two adjacent fit system pads positioned to create curvature for a loop fit system 42. Each of the adjacent fit system pads 40 has a slightly trapezoidal shape to create curvature when placed adjacent to one another. The number of fit system pads 40 used has a direct relationship with the smoothness of the curve.

Figure 7:
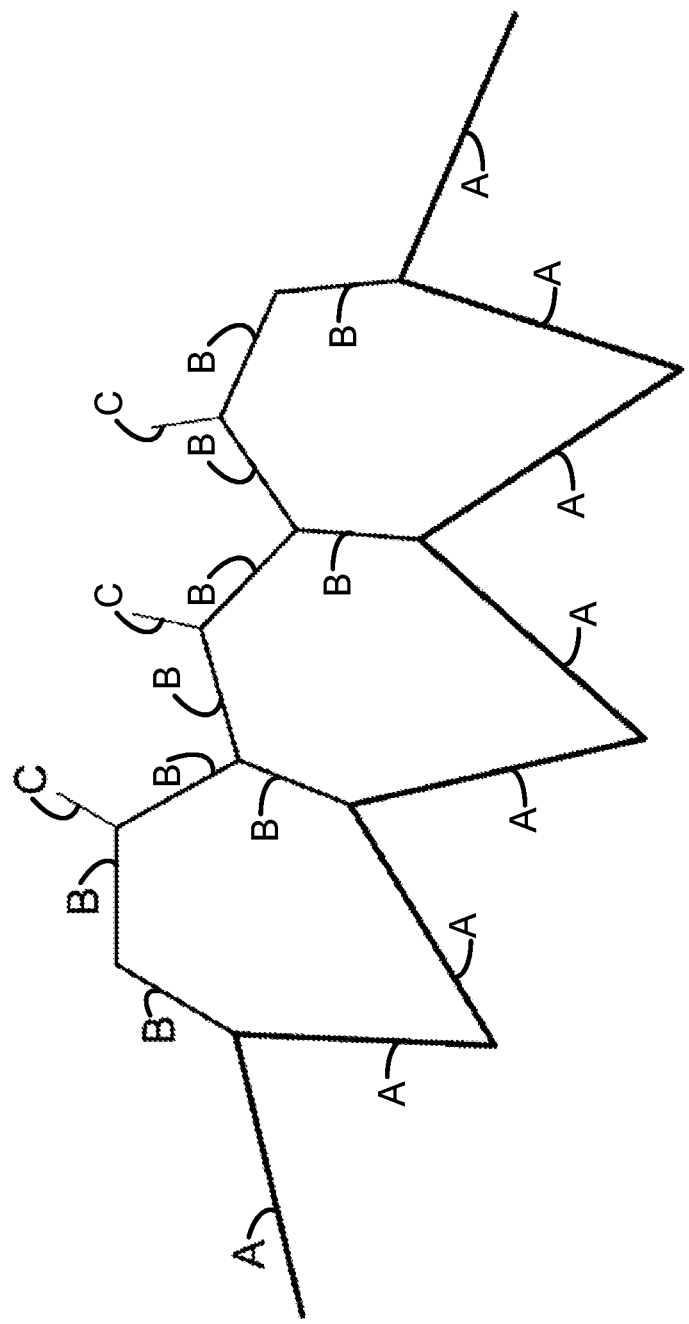
FIG. 7 is an illustration of a two-dimensional curved lattice.

FIG. 7 is an illustration of a two-dimensional curved lattice. In some embodiments, the collapsible beam lattice is designed to create a loop. One manner of constructing a curved lattice is to reduce the length of beams in layers closer to the center of the loop and the user's head. Pictured in FIG. 7 is the lattice of FIG. 1 constructed as a curved lattice. The lattice of FIG. 7 uses three different beam lengths (A-C). The base of the lattice has the longest beam length (A). The beam lengths decrease in each progressive, upward layer. This lattice pattern causes tighter angles in each hexagonal cell thereby creating a curved lattice.

Figure 8:
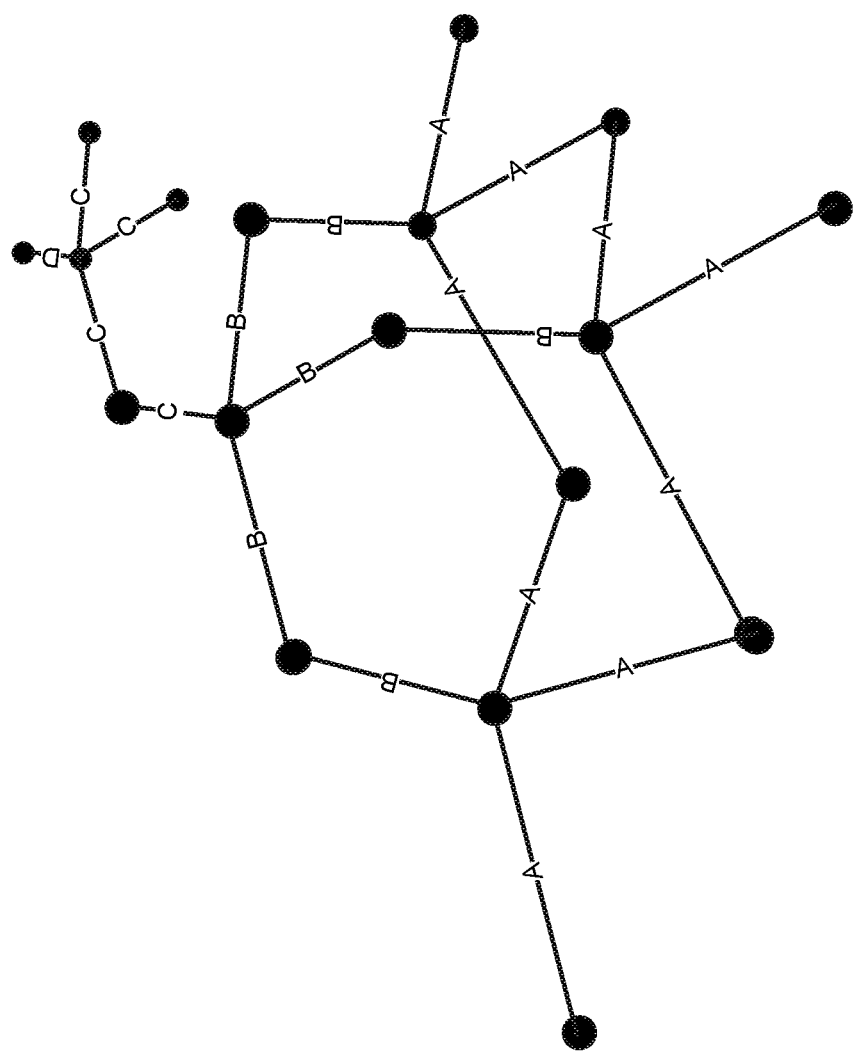
FIG. 8 is an illustration of a three-dimensional curved lattice.

FIG. 8 is an illustration of a three-dimensional curved lattice. The example of FIG. 7 may be constructed as a tetrahedral lattice as well. In a tetrahedral lattice, on a bottom layer of the fit system pad 40, three beams generally pointing downward (connected to a given node) are at a first length (A), and the fourth beam generally pointing up is slightly shorter (B). In the next higher layer of the fit system pad 40, the corresponding three beams pointing down are the "slightly shorter" length (B). The fourth beam pointing upward in the second layer is shorter still (C). Repeating this pattern will generally cause curvature in the lattice.

The greater the variation in beam length across each layer will increase the curvature in the lattice. In these embodiments, the repeating pattern of the lattice is greater than a single node, and includes a series of layers at progressively smaller sizes. This technique can be employed in most elemental atomic lattices and molecular lattices thereby creating a curved atomic lattice or a curved molecular lattice.

Figure 9:
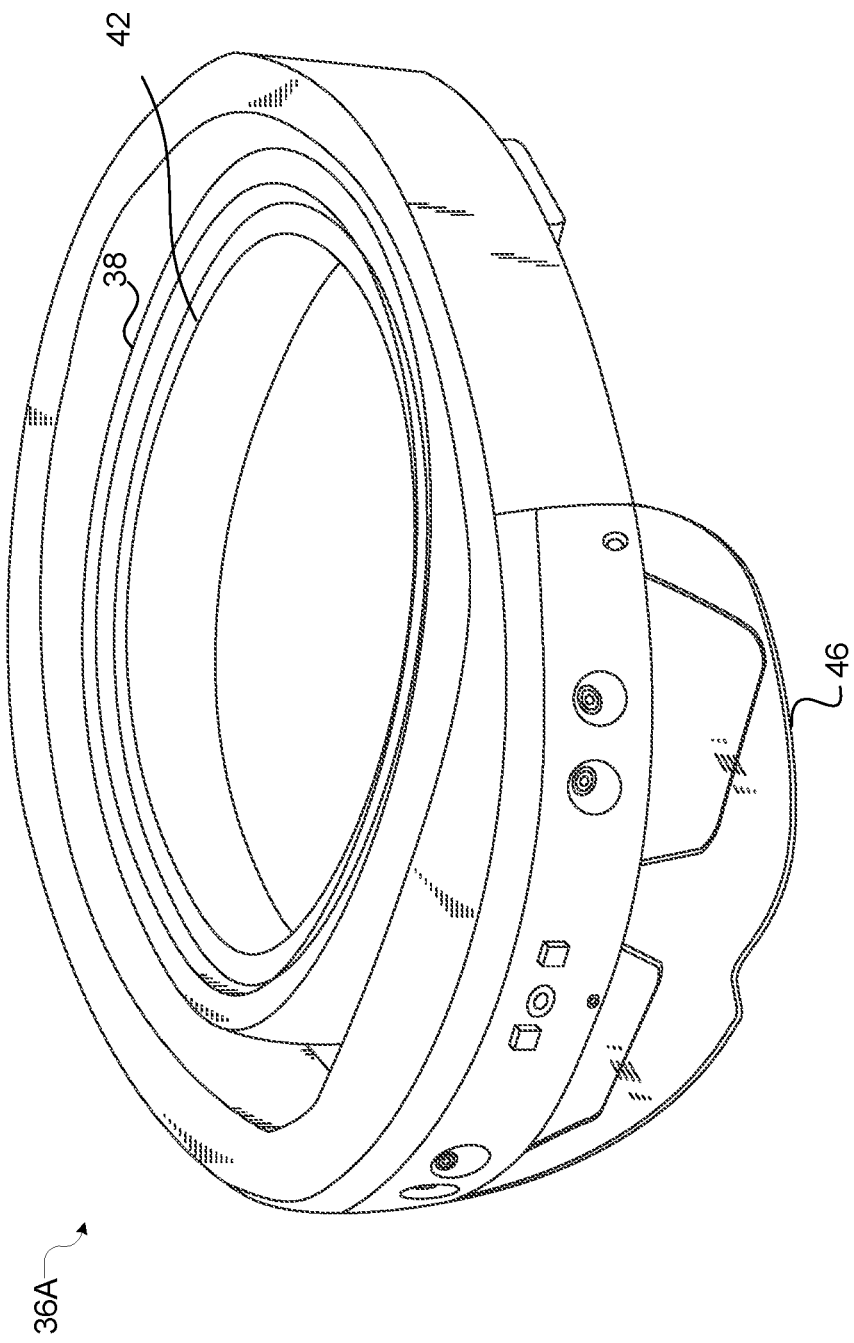
FIG. 9 is an illustration of a head mounted display head article.

FIG. 9 is an illustration of a head mounted display ("HMD") device 36A. Head mounted display devices (such as the Hololens marketed by Microsoft Corporation of Redmond, Wash.) including near-eye displays 46 can be benefited by inclusion of a comfort system designed to maintain a stable center of gravity while also providing contented comfort for the users. HMD device designers often make a trade-off between comfort level and the amount of compression made around the human head when mounting and tightening the device to ensuring safe fit without slippage. Tuning and tightening is different for various users and depends on the specific shape and nature of the billions of human heads. As a result, a traditional HMD comfort system has more pressure points for certain users than for others. Otherwise, the HMD device 36A is prone to the undesired event of falling or slipping from the head. This is particularly an issue where a given device, such as the HMD 36A, is likely to be used for long periods of time.

The fit system 20 illustrated in FIG. 9 makes use of a loop system 42. However, the fit system displayed in FIG. 5 is also suitable. The rigid frame 38 displayed has an annular shape, though other shapes are also suitable (e.g., over-the-head support, or full cap).

Figure 10:
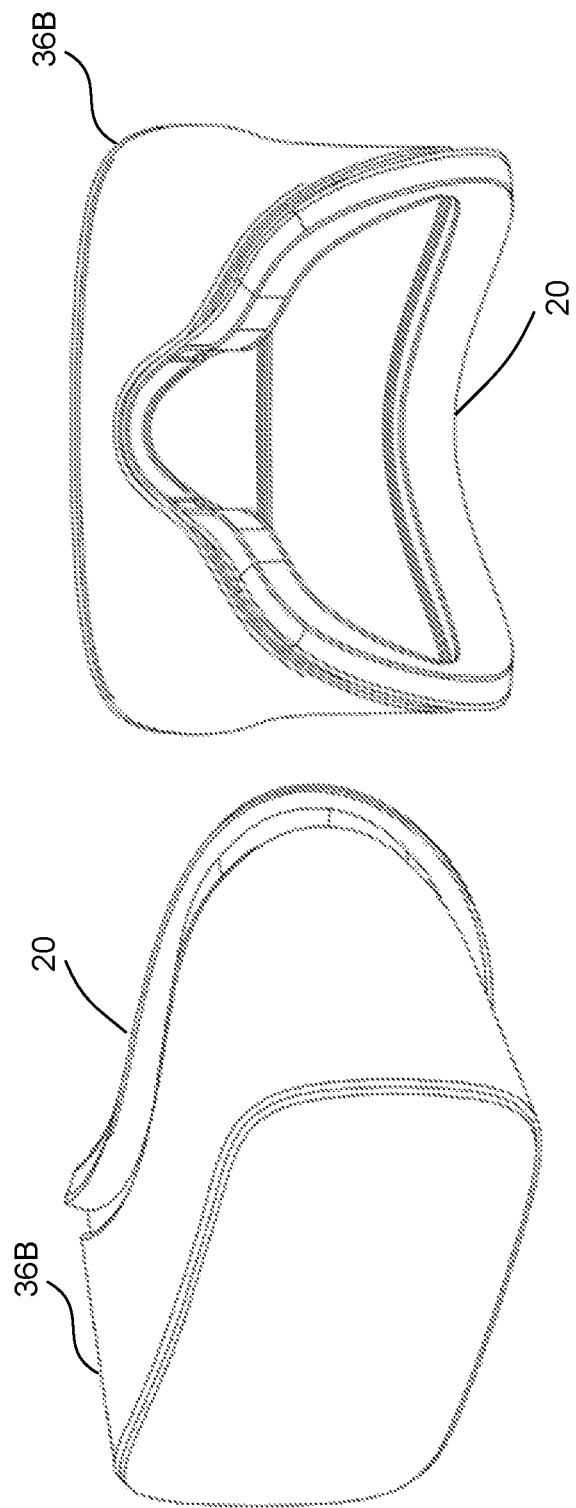
FIG. 10 is an illustration of a mask head article with a goggle configuration.

The loop fit system 42 may also integrate with other styles of HMDs such as a goggle configuration 36B. FIG. 10 is an illustration of a mask head article with a goggle configuration 36B. In such a configuration, the fit system 20 can line the front of the face of the user. The goggle configuration mask 36B may also make use of a head strap to secure the goggle configuration mask 36B to the head. Goggle configuration masks 36B may be HMDs or wearable goggles.

Figure 11:
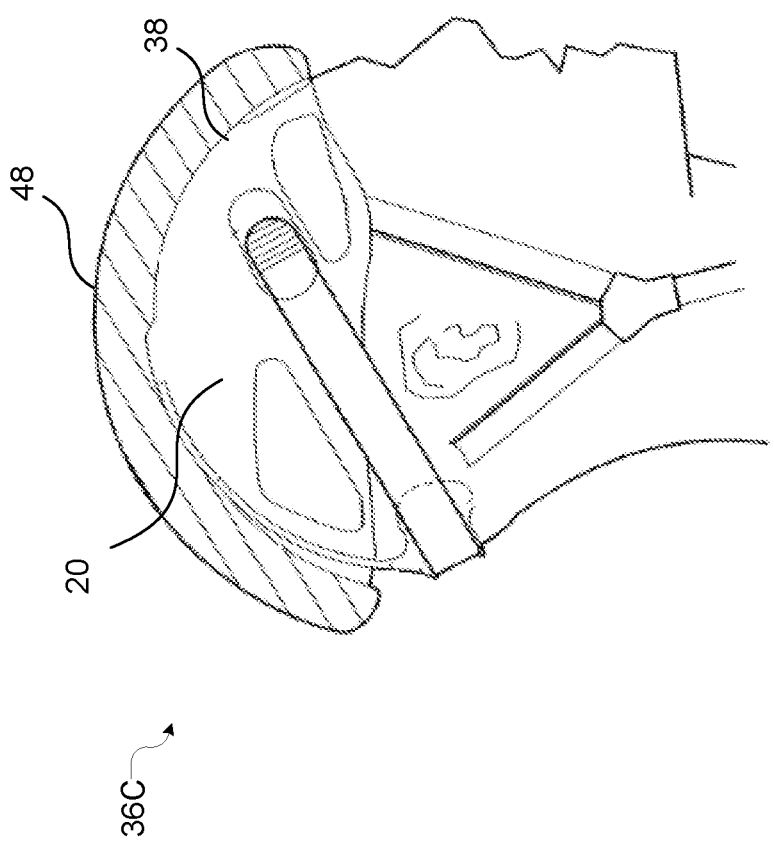
FIG. 11 is an illustration of a helmet-style head article.

FIG. 11 is an illustration of a helmet-style head article 36C. The fit system 20 may also be incorporated into helmets such as bicycle helmets, hardhats, or combat protection. Helmet-style head articles 36C additionally include a helmet shell 48. The fit system 20 integrates with the rigid shell 38 of a helmet article 36 of C in the same manner that traditional pattern is positioned on helmets.

EXAMPLES OF CERTAIN EMBODIMENTS

1. An apparatus comprising: a frame configured to be worn on a body part of a user and a cushion material mounted to the frame so as to be positioned against the user's body part when the apparatus is worn by the user, the cushion material including a repeating pattern of collapsible beams that causes the cushion material to produce a substantially constant reactive pressure in response to compression of the cushion material over a specified range of compression values.

2. The apparatus of example 1, wherein the frame is configured to support the body part of the user on two opposite sides of the body part.

3. The apparatus any of examples 1 to 2, wherein the repeating pattern of collapsible beams is an atomic or molecular lattice.

4. The apparatus any of examples 1 to 3, wherein the frame is ring shaped.

5. The apparatus any of examples 1 to 4, wherein the repeating pattern of collapsible beams is a curved atomic or molecular lattice.

6. The apparatus any of examples 1 to 5, wherein the body part is a user's head and the cushion material is positioned to contact the user's head on a front side of the user's head and a back side of the user's head.

7. The apparatus any of examples 1 to 6, wherein the body part is a user's head and the cushion material is constructed as a curved loop and positioned by the frame to contact a circumference of the user's head.

8. The apparatus any of examples 1 to 7, wherein the body part is a user's head and the cushion material is constructed of a plurality of pieces mounted on the frame and positioned to contact a circumference of the user's head.

9. The apparatus any of examples 1 to 8, further comprising: a near-eye-display affixed to the frame.

10. The apparatus of any of examples 1 to 9, wherein the specified range of compression values is perceivable by a human sensory system.

11. The apparatus any of examples 1 to 10, further comprising: a protective helmet shell affixed to the frame.

12. An apparatus comprising: a near eye display that is worn on a user's head with a frame that adjusts to a variable head size of a wearer; and a cushion material mounted to the frame so as to be positioned against the user's head when the apparatus is worn by the user, the cushion material including collapsible beams that causes the cushion material to produce a substantially constant reactive pressure in response to compression of the cushion material over a specified range of compression values.

13. The apparatus of example 12, wherein the collapsible beams further comprise a lattice of multiple layers and wherein increasing compression values substantially collapse a single layer of the multiple layers at a time.

14. The apparatus any of examples 12 to 13, wherein collapsible beams are arranged in a repeating pattern that exhibits a range of compression values having a disproportionate relationship to compression pressure.

15. The apparatus any of examples 12 to 14, wherein the cushion material is constructed of a plurality of pieces mounted on the frame and positioned surrounding the user's head.

16. The apparatus any of examples 12 to 15, wherein by varying a length, a diameter, and a support condition of the collapsible beams, the consistent pressure is maintained at substantially half a pound per square inch over the range of compression values.

17. The apparatus any of examples 12 to 16, wherein by varying a length, a diameter, and a support condition of the collapsible beams, the range of compression values varies at least ten millimeters while maintaining the consistent pressure.

18. The apparatus any of examples 12 to 17, wherein the collapsible beams of the cushion material is 3-D printed elastomeric foam.

19. An apparatus comprising: a frame configured to be worn by a user on the user's head; and a cushion material mounted to the frame so as to be positioned against a plurality of locations on the user's head when the apparatus is worn by the user, the cushion material including foam that exhibits a range of compression values having a disproportionate relationship to compression pressure and distributes pressure evenly across said range of compression values.

20. The apparatus of example 19, wherein the cushion material is constructed as a curved loop and positioned by the frame to contact a circumference of the user's head.

Any or all of the features and functions described above can be combined with each other, except to the extent it may be otherwise stated above or to the extent that any such embodiments may be incompatible by virtue of their function or structure, as will be apparent to persons of ordinary skill in the art. Unless contrary to physical possibility, it is envisioned that (i) the methods/steps described herein may be performed in any sequence and/or in any combination, and that (ii) the components of respective embodiments may be combined in any manner.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims, and other equivalent features and acts are intended to be within the scope of the claims.

What is claimed is:

1. An apparatus comprising:
a frame configured to be worn on a body part of a user; and
a cushion mounted to the frame at a frame contact surface and extending to a body contact surface opposite the frame contact surface so as to be configured to be positioned between the frame and the body part of the user when the apparatus is worn by the user, the cushion including a curved two-dimensional lattice configured to produce a substantially constant reactive pressure in response to compression of the cushion over a range of compression values, the curved two-dimensional lattice including:
a plurality of rows of hexagons;
a first repeating pattern of collapsible beams having a first length and forming at least one side of each hexagon in a first row of hexagons,
a second repeating pattern of collapsible beams having a second length greater than the first length, forming at least one side of each hexagon in the first row of hexagons, and forming at least two sides of each hexagon in a second row of hexagons farther from the body contact surface than the first row of hexagons, and
a third repeating pattern of collapsible beams having a third length greater than the second length, forming at least one side of each hexagon of the second row of hexagons, and forming at least one side of each hexagon in a third row of hexagons farther from the body contact surface than the second row of hexagons.

2. The apparatus of claim 1, wherein the frame is configured to support the body part of the user on two opposite sides of the body part.

3. The apparatus of claim 2, wherein the frame is ring shaped.

4. The apparatus of claim 3, wherein the first, second, and third repeating patterns of collapsible beams form a curved atomic or molecular lattice.

5. The apparatus of claim 2, wherein the body part is a user's head and the cushion is configured to contact the user's head on a front side of the user's head and a back side of the user's head when the apparatus is worn by the user.

6. The apparatus of claim 2, wherein the body part is a user's head and the cushion is constructed as a curved loop and configured to contact a circumference of the user's head when the apparatus is worn by the user.

7. The apparatus of claim 2, wherein the body part is a user's head and the cushion includes a plurality of pieces mounted on the frame and configured to contact a circumference of the user's head when the apparatus is worn by the user.

8. The apparatus of claim 1, wherein the range of compression values is perceivable by a human sensory system.

9. An apparatus comprising:
a frame configured to be worn by a user on a head of the user; and
a cushion mounted to the frame at a frame contact surface and extending to a body contact surface opposite the frame contact surface so as to be configured to be positioned between the frame and a plurality of locations on the head of the user when the apparatus is worn by the user, the cushion including a curved two-dimensional lattice configured to exhibit a range of compression values having a disproportionate relationship to compression pressure and distribute pressure evenly across the range of compression values, the curved two-dimensional lattice including:
a plurality of rows of hexagons;
a first repeating pattern of collapsible beams having a first length and forming at least one side of each hexagon in a first row of hexagons,
a second repeating pattern of collapsible beams having a second length greater than the first length, forming at least one side of each hexagon in the first row of hexagons, and forming at least two sides of each hexagon in a second row of hexagons farther from the body contact surface than the first row of hexagons, and
a third repeating pattern of collapsible beams having a third length greater than the second length, forming at least one side of each hexagon of the second row of hexagons, and forming at least one side of each hexagon in a third row of hexagons farther from the body contact surface than the second row of hexagons.

10. The apparatus of claim 9, wherein the cushion is constructed as a curved loop and configured to contact a circumference of the head of the user when the apparatus is worn by the user.

11. The apparatus of claim 9, wherein the cushion is configured to contact the user's head on a front side of the user's head and a back side of the user's head when the apparatus is worn by the user.

12. The apparatus of claim 9, wherein the cushion includes a plurality of pieces mounted on the frame and configured to contact a circumference of the user's head when the apparatus is worn by the user.

13. A head-mounted display device comprising:
a frame configured to be worn on a head of a user; and
a cushion mounted to the frame at a frame contact surface and extending to a head contact surface opposite the frame contact surface so as to be configured to be positioned between the frame and the head of the user when the head-mounted device is worn by the user, the cushion including a curved two-dimensional lattice of hexagons including:
a first layer of hexagons;
a first pattern of collapsible beams having a first length and forming at least one side of each hexagon in the first layer of hexagons;
a second layer of hexagons farther from the head contact surface than the first layer of hexagons; and
a second pattern of collapsible beams having a second length greater than the first length and forming a shared side of a hexagon of the first layer of hexagons and a hexagon of the second layer of hexagons.

14. The head-mounted display device of claim 13, wherein the curved two-dimensional lattice of hexagons includes a third layer of hexagons farther from the head contact surface than the second layer of hexagons; and a third pattern of collapsible beams having a third length greater than the second length and forming a shared side of a hexagon of the second layer of hexagons and a hexagon of the third layer of hexagons.

15. The head-mounted device of claim 13, wherein the cushion is constructed as a curved loop and configured to contact a circumference of the head of the user when the head-mounted device is worn by the user.

16. The head-mounted device of claim 13, wherein the cushion is configured to contact the user's head on a front side of the user's head and a back side of the user's head when the head-mounted device is worn by the user.

17. The head-mounted device of claim 13, wherein the cushion includes a plurality of pieces mounted on the frame and configured to contact a circumference of the user's head when the head-mounted device is worn by the user.

* * * * *